(12) United States Patent
Kasowski

(10) Patent No.: US 6,268,494 B1
(45) Date of Patent: Jul. 31, 2001

(54) CONDENSED MELAMINE PHOSPHATES

(75) Inventor: Robert Valentine Kasowski, West Chester, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/601,926

(22) PCT Filed: Mar. 10, 1999

(86) PCT No.: PCT/US99/05184

§ 371 Date: Aug. 9, 2000

§ 102(e) Date: Aug. 9, 2000

(87) PCT Pub. No.: WO99/46250

PCT Pub. Date: Sep. 16, 1999

Related U.S. Application Data

(60) Provisional application No. 60/077,536, filed on Mar. 11, 1998.

(51) Int. Cl.[7] ................................................. C07D 251/66
(52) U.S. Cl. ............................................................ 544/195
(58) Field of Search ................................................ 544/195

(56) References Cited

U.S. PATENT DOCUMENTS

| 3,371,992 | 3/1968 | Shen | 23/165 |
|---|---|---|---|
| 3,453,075 | 7/1969 | Shen | 23/165 |
| 3,635,970 | * 1/1972 | Fessler et al. | 544/195 |
| 3,914,193 | * 10/1975 | Fessler et al. | 544/195 |
| 4,088,752 | * 5/1978 | Muhlemann et al. | 424/57 |
| 4,122,162 | 10/1978 | Muehlemann | 424/52 |
| 4,950,787 | * 8/1990 | Tomko et al. | 544/195 |

FOREIGN PATENT DOCUMENTS

| 0 413 376 | * 2/1991 | (EP) . | |
| 8-48508 | 2/1996 | (JP) | C01B/25/38 |

OTHER PUBLICATIONS

Kirk–Othmer Encyopedia of Chemical Technology 3rd edition, vol. 17, 448–453, 19??.*

* cited by examiner

*Primary Examiner*—John M. Ford
*Assistant Examiner*—Venkataraman Balasubramanian

(57) ABSTRACT

This invention relates to a novel process for the preparation of condensed melamine phosphates, and to melamine pyrophosphate prepared by this process having improved thermal stability as a flame retardant.

4 Claims, 5 Drawing Sheets

CONDENSED MELAMINE PHOSPHATES

CROSS REFERENCE TO RELATED APPLICATIONS

This application is a national filing under 35 U.S.C. 371of International Application No. PCT/US99/05184, filed Mar. 10, 1999, which claims priority benefit of U.S. Provisional No. 60/077,536, filed Mar. 11, 1998.

FIELD OF THE INVENTION

This invention relates to a novel process for the preparation of condensed melamine phosphates, and to melamine pyrophosphate prepared by this process having improved thermal stability as a flame retardant.

BACKGROUND OF THE INVENTION

Melamine pyrophosphate is widely used as a flame retardant additive in paints, coatings, and extruded plastics such as polyamides, polyesters, and polyolefins. In extruded plastics, the stability of the melamine pyrophosphate is important. Decomposition of contaminants, such as melamine orthophosphate, at extrusion temperatures, leads to the evolution of gases and vapors causing foaming and other effects adversely affecting the quality of the extruded product and the efficiency of the flame retardant properties. The thermal stability of melamine pyrophosphate samples is conveniently measured by thermogravimetric analysis (TGA). TGA analyses typically show the weight % loss of the test sample versus temperature as the temperature is increased at a constant rate, e.g., 10°C/min. Additionally, the derivatives of the TGA curve may be plotted, showing the rate of weight loss as weight % loss/min.

Melamine pyrophosphate is conventionally prepared by heating an aqueous slurry of 2 moles of melamine in 4 moles of hydrochloric acid at 80°C to 90°C, forming a solution of melamine dihydrochloride. One mole of tetrasodium pyrophosphate is added, the temperature maintained for about 30 minutes, and the slurry quenched. The precipitated melamine pyrophosphate must be thoroughly washed to remove the by-product sodium chloride and dried. The process is described by Fessler in U.S. Pat. No. 3,914,193. However, the pyrophosphate ion is reported (Corbridge, D.E.C., Structural Chemistry of Phosphorus, Elsevier Scientific Publishing Co., New York, N.Y., 1974, p. 128) to decompose to orthophosphate at low pH and at elevated temperature, i.e., under the conditions necessary for the reaction between melamine dihydrochloride and tetrasodium pyrophosphate. At polymer extrusion temperatures that can exceed 300°C, melamine orthophosphate is less stable than melamine pyrophosphate. The presence of residual sodium and chloride ions also reduces the stability of melamine pyrophosphate under melt extrusion conditions.

Melamine pyrophosphate when prepared according to the methods of the prior art, has borderline stability when used in higher temperature melt extrusion, for instance in polyamide extrusions, due to impurities such as melamine orthophosphate. Efforts to minimize "hot spots", where decomposition of the melamine pyrophosphate flame retardant can occur in the extruder, have included methods to improve the dispersability of melamine pyrophosphate.

Muehlemann and Schmid, in U.S. Pat. No. 4,088,752, and subsequently in U.S. Pat. No. 4,122,162, disclose the preparation of various organic basesalts of oxo-acids of phosphorus and mixed salts of oxo-acids of phosphorus and hydrofluoric acid by passing a salt of the oxo acid through a cation exchange resin and mixing the effluent with an alcoholic solution of an amine, such as an ethoxylated amine, or an alcoholic solution of the amine monohydrofluoride. The salts are isolated by evaporation of the solvent or by the addition of another solvent such as acetone. The technique is not applicable to the preparation of melamine condensed phosphates, and the use of organic solvents is undesirable.

Watanabe, in Japanese Kokai Patent Hei-8-48508 prepared guanidine cyclo-6-phosphate (guanidine hexametaphosphate) by passing a solution of lithium cyclo-6-phosphate through a cation exchange resin and adding to the cooled resulting solution a solution of guanidine phosphate or guanidine carbonate. The product precipitated on standing and was isolated by filtration and washing with acetone. While improving the purity of the cyclo-6-phosphate, Watanabe uses a solution of the organic base, corresponding to the use of melamine hydrochloride in Fessler's process above.

It is desirable to improve the thermal stability and purity of condensed phosphates in general, and for melamine pyrophosphate for use as a flame retardant in the melt processing of polymers in particular, and to improve the manufacturing process. The present invention provides such a process and melamine pyrophosphate with improved stability and enhanced flame retardant properties.

SUMMARY OF THE INVENTION

The present invention comprises a process for preparation of condensed phosphate salts of melamine comprising: a) contacting a solution of an alkali metal condensed phosphate with an acidic ion exchange resin at a temperature of 0°C to ambient to yield condensed phosphoric acid, and b) adding the condensed phosphoric acid at 0°C to ambient temperature to a slurry or suspension of melamine to yield the corresponding melamine condensed phosphate.

The present invention further comprises a compound which is melamine pyrophosphate having a ratio of X-ray diffraction intensities for Peak A:Peak B equal to or larger than 0.25. Peak A occurs at a powder diffraction angle (PDA) of 8.2–8.3 and Peak B occurs at a PDA of 17.8–18.1. The present invention further comprises a composition comprising the melamine pyrophosphate described above and at least one polymer selected from the group consisting of a polyester, polyamide, and polyolefin.

DETAILED DESCRIPTION OF THE INVENTION

The present invention comprises an ion exchange process for the preparation of condensed phosphates of melamine. The term "condensed phosphate" is used herein to describe salts of di- or pyrophosphoric acid ($H_4P_2O_7$), triphosphoric acid ($H_5P_3O_{10}$), polyphosphoric acids $[H_{(m+2)}P_mO_{(3m+1)}]$ wherein m is greater than 3, and the metaphosphoric acids $(HPO_3)_n$ wherein n is equal to or greater than 3, such as trimetaphosphoric $(HPO_3)_3$, tetrametaphosphoric acid $(HPO_3)_4$, and hexametaphosphoric acid $(HPO3)_6$. The term "condensed phosphoric acid" is used herein to describe the corresponding free acids.

The invention also comprises a novel form of melamine pyrophosphate having enhanced stability under the conditions of melt extrusion of plastics such as polyamides, polyesters, polyolefins, and blends of these polymers such as polyamide/polyolefin. The term "melamine pyrophosphate IX" is hereinafter used to describe melamine pyrophosphate prepared by the ion exchange method of the present invention. The melamine pyrophosphate IX of this invention is characterized by showing a significantly different X-ray powder crystallographic analysis pattern. The process of the present invention provides a melamine pyrophosphate IX showing improved performance as measured by mechanical and flame retardancy properties compared with melamine pyrophosphate prepared by the prior art. The melamine pyrophosphate IX is also essentially free of the sodium, chloride, and other phosphate salts characteristically contaminating the melamine pyrophosphate of the prior art. FIGS. 1 through 4 are X-ray diffraction powder crystallography patterns, repared by Test Method 1, comparing melamine pyrophosphate IX (Example 1) and commercially available melamine pyrophosphate samples (Comparative xamples A, B, and C). The powder pattern is obtained from the melamine pyrophosphate IX as produced, without grinding prior to the X-ray analysis. Each peak is identified by the powder diffraction angle shown on the abscissa, and a relative intensity shown on the ordinate. The relative intensity of each peak (i) is conventionally displayed relative to the strongest peak (imax). The strongest peak is assigned the value 100. The ratio of the relative intensities at powder diffraction angle values of 8.2 to 8.3 and 17.9 to 18.1 are used to characterize the product of this invention. Numerical values for melamine pyrophosphate IX prepared by the process of this invention and commercially available Comparative Examples A, B, and C prepared by the prior art are shown in Table 1.

Figure 5:
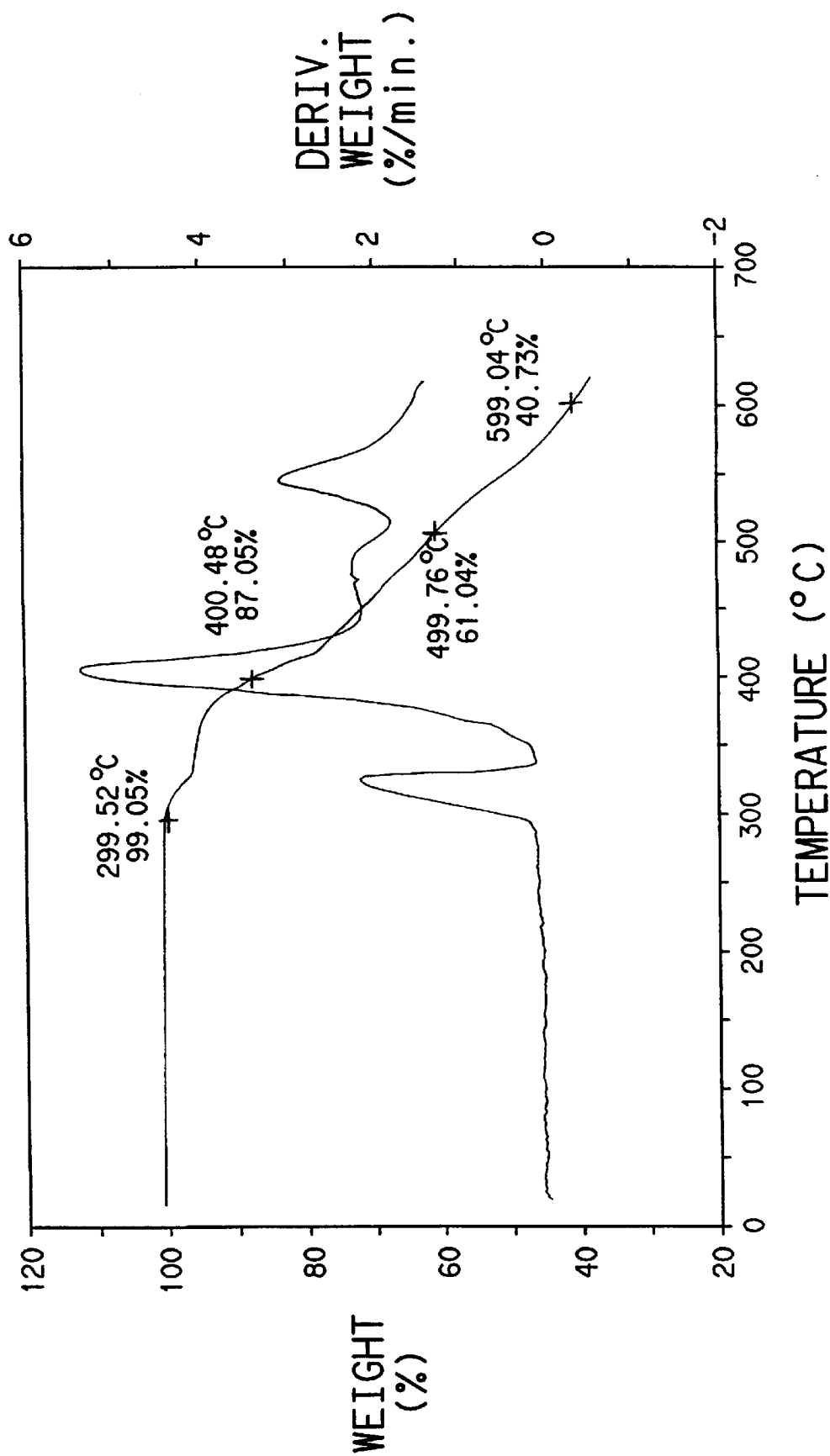
FIG. 5 is a thermogravimetric analysis of the melamine pyrophosphate of Example 1.

FIG. 5 shows a thermogravimetric analysis (TGA) plot of melamine pyrophosphate IX prepared by the process of this invention. Curve C is the standard TGA plot, showing weight vs. temperature, and Curve D shows the derivative as weight %/minute vs. temperature).

The process of this invention produces melamine pyrophosphate IX with characteristically different X-ray crystallographic properties compared with melamine pyrophosphate of the prior art. Such differences indicate different crystalline structures. While many X-ray peaks are common to all the samples, relative intensity differences distinguish the products. As shown in FIGS. 1 through 4 and Table 1, melamine pyrophosphate IX is characterized by a prominent peak at a powder diffraction angle of 8.2–8.3 (marked as Peak A in the Figures). Specifically, the relative intensity of the Peak A can be compared with the common large peak at 17.9–18.1 (marked as Peak B in the Figures). In the case of the melamine pyrophosphate IX, the ratio of relative intensities of Peak A:Peak B is 37/100, or 0.37. This ratio is substantially smaller for Comparative Examples A, B, and C. The improved melamine pyrophosphate IX of this invention is characterized by showing a Peak A:Peak B ratio equal to or greater than 0.25. The high value of this ratio is characteristic of the different orientation of melamine pyrophosphate IX.

TABLE 1

Powder Diffraction Angles (PDA) and Relative Intensities for Major Peaks (Test Method 1)

| | | Commercially Available Melamine Pyrophosphate | | | | | |
|---|---|---|---|---|---|---|---|
| Example 1 | | Comparative Example A | | Comparative Example B | | Comparative Example C | |
| PDA | i/imax | PDA | i/imax | PDA | i/imax | PDA | i/imax |
| 8.2* | 37 | 8.3* | 14 | 8.2* | 9 | 8.2* | 8 |
| 12.0 | 7 | 12.1 | 11 | 12.1 | 11 | 12.1 | 6 |
| 16.4 | 14 | 16.7 | 29.2 | 16.7 | 35 | 16.7 | 40 |
| 17.9** | 100 | 18.1** | 88.5 | 18.1** | 70 | 18.0** | 100 |
| 18.9 | 41 | 18.9 | 32.3 | 19.0 | 31 | 18.9 | 17 |
| | | 19.7 | 7 | 19.7 | 7 | | |
| 24.1 | 7 | 24.2 | 11 | 23.8 | 11 | | |
| 24.8 | 10 | 24.8 | 9 | 24.3 | 11 | | |
| | | | | 24.9 | 7 | | |
| 25.2 | 10 | 25.3 | 6 | 25.3 | 7 | 25.7 | 29 |
| 25.6 | 60 | 25.7 | 43 | 25.7 | 32 | 26.0 | 24 |
| | | 26.0 | 18 | 26.0 | 20 | | |
| | | | | 26.3 | 9 | | |
| 27.4 | 24 | 27.5 | 100 | 27.5 | 100 | 27.5 | 45 |
| | | 28.5 | 16 | 28.0 | 9 | | |
| | | | | 24.4 | 15 | | |
| 33.2 | 18 | 31.8 | 10 | 31.8 | 13 | | |
| | | 33.2 | 12 | 32.4 | 7 | | |
| | | | | 33.3 | 8 | | |
| 42.1 | 14 | 42.2 | 16 | 42.2 | 11 | 42.2 | 8 |
| Ratio of Peak A to Peak B | | | | | | | |
| 0.37 | | 0.16 | | 0.13 | | 0.08 | |

*Peak A
**Peak B

The process of the present invention comprises the steps of a) contacting a solution of an alkali metal condensed phosphate with an acidic ion exchange resin to yield condensed phosphoric acid, and b) adding the condensed phosphoric acid to a slurry or suspension of melamine to yield the corresponding melamine condensed phosphate.

The process of this invention is conducted at 0°C to ambient temperature.

The alkali metal condensed phosphate employed is typically tetrasodium pyrophosphate or tetrapotassium pyrophosphate, although other salts are suitable for use herein. Step a) of the process removes the cation from the solution of the condensed phosphate salt to yield condensed phosphoric acid by contacting the solution with the acid form of a strongly acid cation exchange resin. In step b) the condensed phosphoric acid is immediately reacted with an aqueous slurry or suspension of melamine to yield the corresponding melamine condensed phosphate. Step b) is completed before hydrolysis of the acid can occur. The condensed phosphate is separated conventionally, e.g., by filtration or centrifugation, washed with cold water, and dried conventionally.

An unexpected result of the process of the present invention is the ability of the water-insoluble melamine fully to react with the pyrophosphoric acid solution at room temperature and at a pH greater than 2.5.

Among the advantages of the process of this invention is the fact that the salts are produced essentially free of other anions formed by hydrolysis of the condensed phosphates. For instance, in the case of melamine pyrophosphate, melamine pyrophosphate IX is obtained essentially free of melamine orthophosphate, a ubiquitous contaminant of melamine pyrophosphate prepared by the prior art process.

Additionally, in comparison with the prior art processes, the process of this invention eliminates the difficult task of removing sodium and chloride ions from products.

The process of this invention is described below in detail for the preparation of melamine pyrophosphate IX from tetrasodium pyrophosphate and melamine. While this specific description utilizes the sodium salt and a column of ion exchange resin, other metal salts and other ion exchange resin configurations such as an ion exchange membrane, may be substituted in the practice of this invention. The entire reaction process is carried out at ambient temperatures or below. Any strong acid cation exchange resin is suitable for use herein. Examples include sulfonic acid resin such as AMBERLITE 120H available from Aldrich Chemical Co., Milwaukee, Wis., or perfluorinated ion exchange polymers such as NAFION®, available from E. I. du Pont de Nemours and Company, Wilmington, Del. The strong acid cation exchange resin is first converted to the acid form by treatment with strong acid, typically 2N hydrochloric acid, and thoroughly washed. Deionized water is used throughout this example of the process of this invention. A 1% to 15% solution, and preferably a 2% to 5% solution, by weight of the tetrasodium pyrophosphate in water is prepared in an amount to contain about 0.5 moles tetrasodium pyrophosphate per mole of melamine. The stoichiometric ratio of tetrasodium pyrophosphate to melamine is maintained between 0.5:0.9 to 0.5:1.1, and preferably 0.5:1.0. The tetrasodium pyrophosphate solution is contacted with the acidic ion exchange resin, for instance by passing the tetrasodium pyrophosphate solution slowly through a bed, membrane or column of the resin, to replace the sodium cations of the tetrasodium pyrophosphate with hydrogen ions to yield pyrophosphoric acid. A slurry containing 1% to 15%, and preferably 2% to 5%, of the melamine in water is prepared, and will typically have an initial pH of about 6 to 8. The melamine is finely divided, with particle size of about 10 um or less. The pyrophosphoric acid solution is immediately passed into the stirred melamine slurry. The ion exchange resin is washed with 1 to 2, and preferably 1, bed volumes of water. A bed volume is an amount of water equal to the volume of ion exchange resin. The washings are also added to the melamine slurry. Clearly the capacity of the resin to remove sodium ions should not be exceeded. The effluent pyrophosphoric acid solution will have a pH of about 1.2 when complete sodium removal is occurring. The pH of the effluent rises when sodium ions are not all removed by the ion exchange resin. The pH should not be allowed to exceed 2.0. A consequence of sodium ion bleed-through from the ion exchange resin is a poorer quality melamine pyrophosphate IX product. Under such undesirable conditions, extraneous diffraction peaks appear in the X-ray analysis indicating an incorrect melamine to pyrophosphate ratio in the product.

After addition of the pyrophosphoric acid solution, agitation of the melamine slurry is continued until the reaction is complete. When the reaction is complete and the reactant molar ratio of tetrasodium pyrophosphate to melamine is about 0.5: 1.0, the pH of the slurry will decrease to about 2.75 to 3.0. Completion of reaction requires longer time as the melamine particle size increases. The melamine pyrophosphate IX product is separated, for instance by filtration or centrifugation. The melamine pyrophosphate IX is washed with water and dried at 80°C to 100°C. The spent ion exchange resin is conventionally regenerated, typically with 2N hydrochloric acid and washed thoroughly with water to remove chloride before reuse.

In cases where a strict stoichiometry ratio of 0.5:1 pyrophosphoric acid:melamine is not accurately maintained, the resulting melamine pyrophosphate IX product will be either rich or deficient in melamine, but is nevertheless characterized by a very low content of orthophosphate impurities and a ratio of Peak A to Peak B of the X-ray diffraction pattern of equal to or greater than 0.25 as previously described. The present invention provides for the production of a pyrophosphate essentially free of orthophosphate, but maintaining exact stoichiometry is not essential for many applications.

The process of this invention provides advantages over the prior art. The melamine pyrophosphate IX of the present invention is substantially free of sodium and chloride ions, the presence of which in the process of the prior art conventionally necessitates exhaustive washing. The pyrophosphate solution is not exposed to high temperatures, and the time the pyrophosphate solution is exposed to low pH values (for instance less than 2) is minimized compared with the extensive exposure to pH values less than 2 associated with the hydrochloric acid used in the preparation of melamine pyrophosphate in the prior art. Elevated temperature and acidic conditions are both conducive to the formation of orthophosphoric acid and thus contaminate the product with melamine orthophosphate. Melamine orthophosphate is known to be less stable than melamine pyrophosphate under polymer melt processing conditions and will evolve water at melt processing temperature with deleterious results on the extruded polymer.

The yield of melamine pyrophosphate IX by the process of this invention is 94% +/− 1%, representing a substantial improvement over the yield of about 80% +− 2% typically obtained when prepared from melamine dihydrochloride and tetrasodium pyrophosphate at elevated temperature according to the prior art. Melamine pyrophosphate prepared according to the prior art requires very extensive washing with water to remove the byproduct sodium chloride. Particularly in the initial stages of washing, while the pH is very low, some loss of melamine pyrophosphate by dissolution occurs.

The melamine pyrophosphate IX of this invention is conventionally blended with the desired synthetic polymers for extrusion with other additives, such as reinforcing glass fiber and plasticizers such as FYROFLEX RDP (available from Akzo Nobel, Dobbs Ferry, N.Y.), with the proportion of melamine pyrophosphate IX added being adjusted to provide the desired level of flame retardancy. The melamine pyrophosphate IX of the present invention is also useful in other applications including intumescent fire and heat retardant paints.

In another embodiment, the melamine pyrophosphate IX of the present invention is optionally mixed or coated with coupling agents such as amino silane and other additives used in conjunction with molding and extrusion, such as lubricants, colorants, heat stabilizers, etc. A variety of such coupling agents and additives are available for various polymers and polymer mixtures, and the suitable selection of such coupling agents and additives is well known to those skilled in the art.

The process of this invention produces melamine pyrophosphate IX and other condensed phosphates having enhanced thermal stability under polymer melt extrusion conditions compared with melamine pyrophosphate of the prior art.

TEST METHODS

The following test methods were employed in the examples hereinafter.

Method 1. X-ray Analysis

The X-ray powder diffraction patterns were prepared using a Phillips diffractometer model 3720 equipped with monochrometer, and using Copper K alpha radiation. The powder pattern was obtained from the melamine pyrophosphate IX as produced, without grinding prior to the X-ray analysis.

Method 2. Underwriters'Laboratories UL-94 Flammability Test

A 5-inch by ½-inch (12.7 by 1.27 cm) molded bar, $\frac{1}{16}^{th}$ inch (0.16 cm) in thickness was mounted vertically and flamed twice (1st and 2nd application) and the duration of the each subsequent burning period measured. The test was made on five bars. A V-0 rating requires a total flaming time from the five tests to be less than 50 seconds, with no bar burning for more than 10 seconds and no ignition of a cotton pad placed below the bar due to melted and burning material.

The full details for the testing procedure and the less stringent requirements for V-1 and V-2 ratings are detailed in the UL-94 Test Specifications.

Method 3. Thermogravimetric Analysis

TGA analyses were performed according to ASTM D 3850-84 (American Society for Testing Materials). The rate of thermal degradation or weight loss was measured at a temperature gradient of 100 °C/min under nitrogen.

Method 4. Measurement of Strength and Elongation

Elongation and tensile strength were measured using ASTM D256.

MATERIALS

The following materials were employed in the Examples.

Melamine and tetrasodium pyrophosphate were obtained from StanChem Co., Stamford Conn.

Commercially available melamine pyrophosphate brand A, brand B, and brand C were obtained from Cytek, Newark, N.J.; StanChem Co., Stamford, Conn.; and Hummel Croton, South Plainfield, N.J.

AMBERLITE 120H ion exchange resin, dipentaerythritol, calcium carbonate, and zinc acetate were obtained from Aldrich Chemical Co., Milwaukee Wis.

A1100 (a silane coupling agent) was obtained from OSI Specialties Danbury, Conn.

ZYTEL® 101 nylon 6,6 and RYNITE® 3934 polyester resins were obtained from E. I. du Pont de Nemours and Company, Wilmington Del.

PPG 3540 and PPG 3563 glass reinforcing agents were obtained from PPG Industries, Pittsburgh Pa.

ACRAWAX C, an extrusion lubricant, was obtained from Lonza, Inc. Fairlawn, N.J.

LOXIOL 7119, an extrusion lubricant, was obtained from Hankel Company, LaGrange, Ill.

EPON 1009F, an extrusion epoxy resin was obtained from Shell Company, Houston Tex.

Standard molding resin grade polypropylene, was obtained from Lyondell Petrochemical Company, Houston Tex.

EXAMPLES

Example 1

Synthesis of Melamine Pyrophosphate IX

Tetrasodium pyrophosphate (110 g) was dissolved in 4.1 l of deionized water at ambient temperature. Melamine (104 g) was separately slurried in 4.1 l of deionized water at ambient temperature. The clear tetrasodium pyrophosphate solution was passed at a rate of 150 ml/min. through a 5 cm inner diameter ion exchange column containing 1.5l of AMBERLITE 120H ion exchange resin. The pyrophosphoric acid solution flowing from the exchange column was passed directly into the melamine slurry container. After agitating for 15 minutes, the product melamine pyrophosphate IX was then recovered by filtration and washed with deionized water (2 l). The product melamine pyrophosphate IX was dried in an oven at 100°C to constant weight. Yields from several preparations were 94% +/− 1%.

Figure 1:
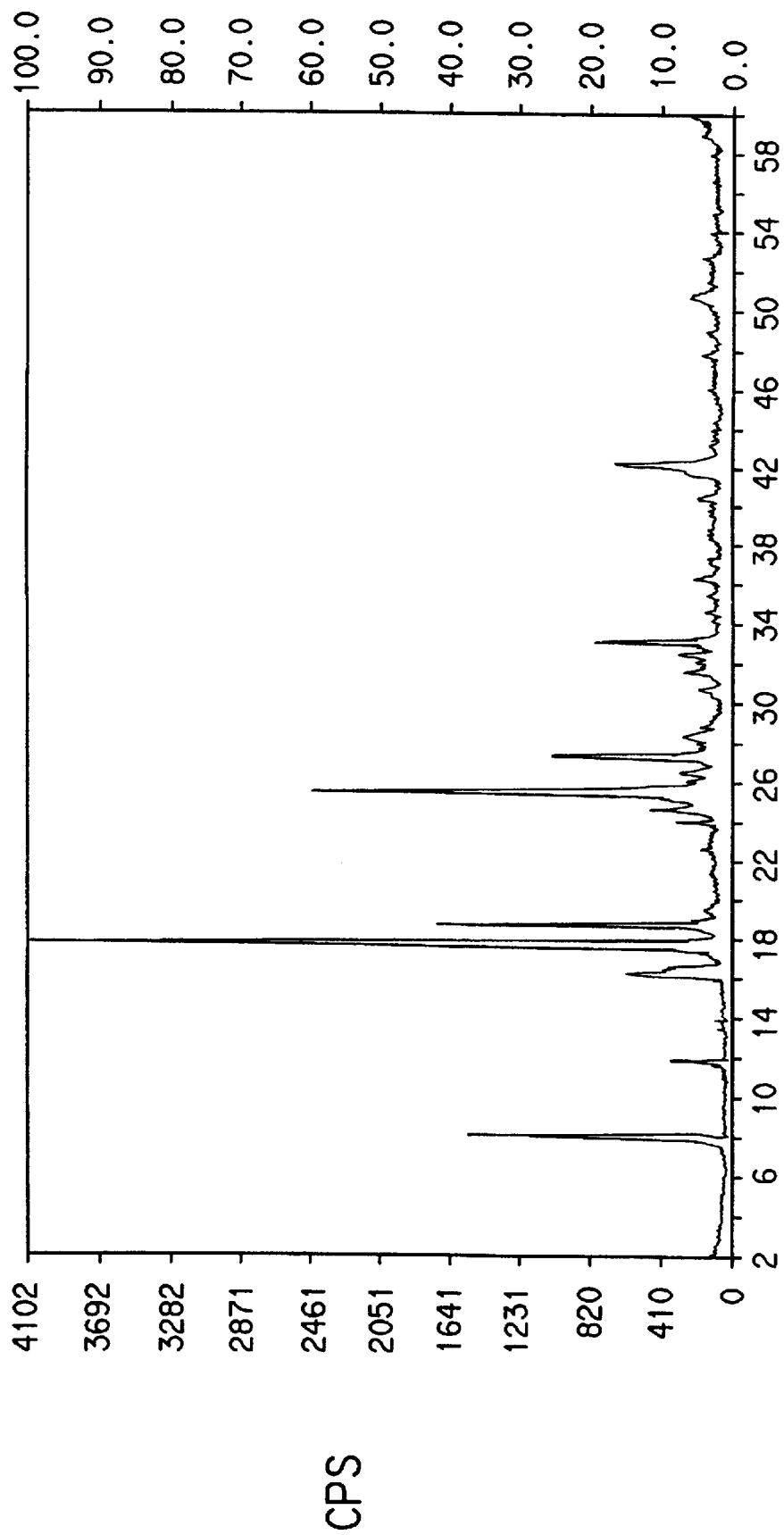
FIG. 1 is an X-ray diffraction pattern of the melamine pyrophosphate of Example 1 (by Test Method 1).
Figure 2:
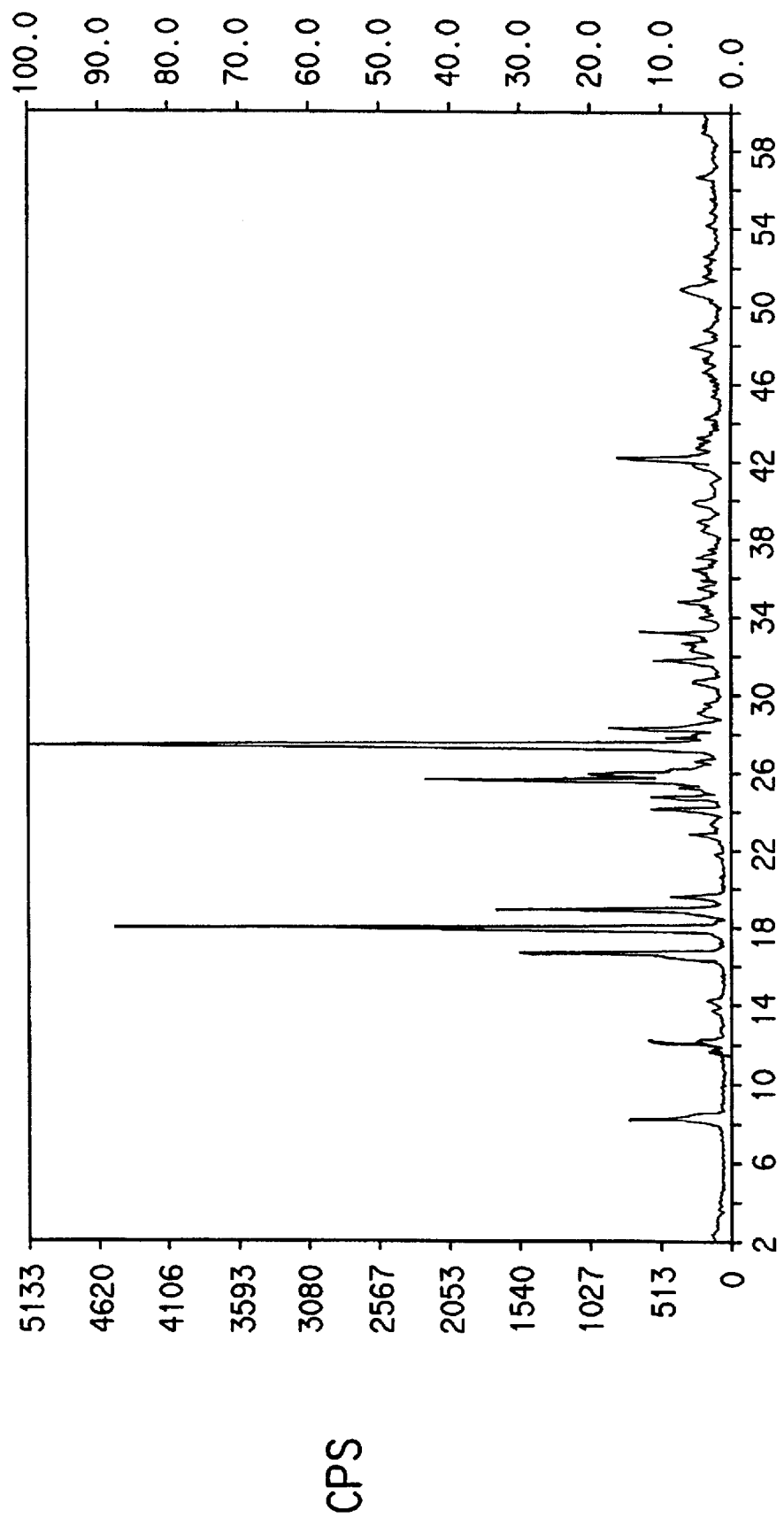
FIG. 2 is an X-ray diffraction pattern of commercially available melamine pyrophosphate of brand A.
Figure 3:
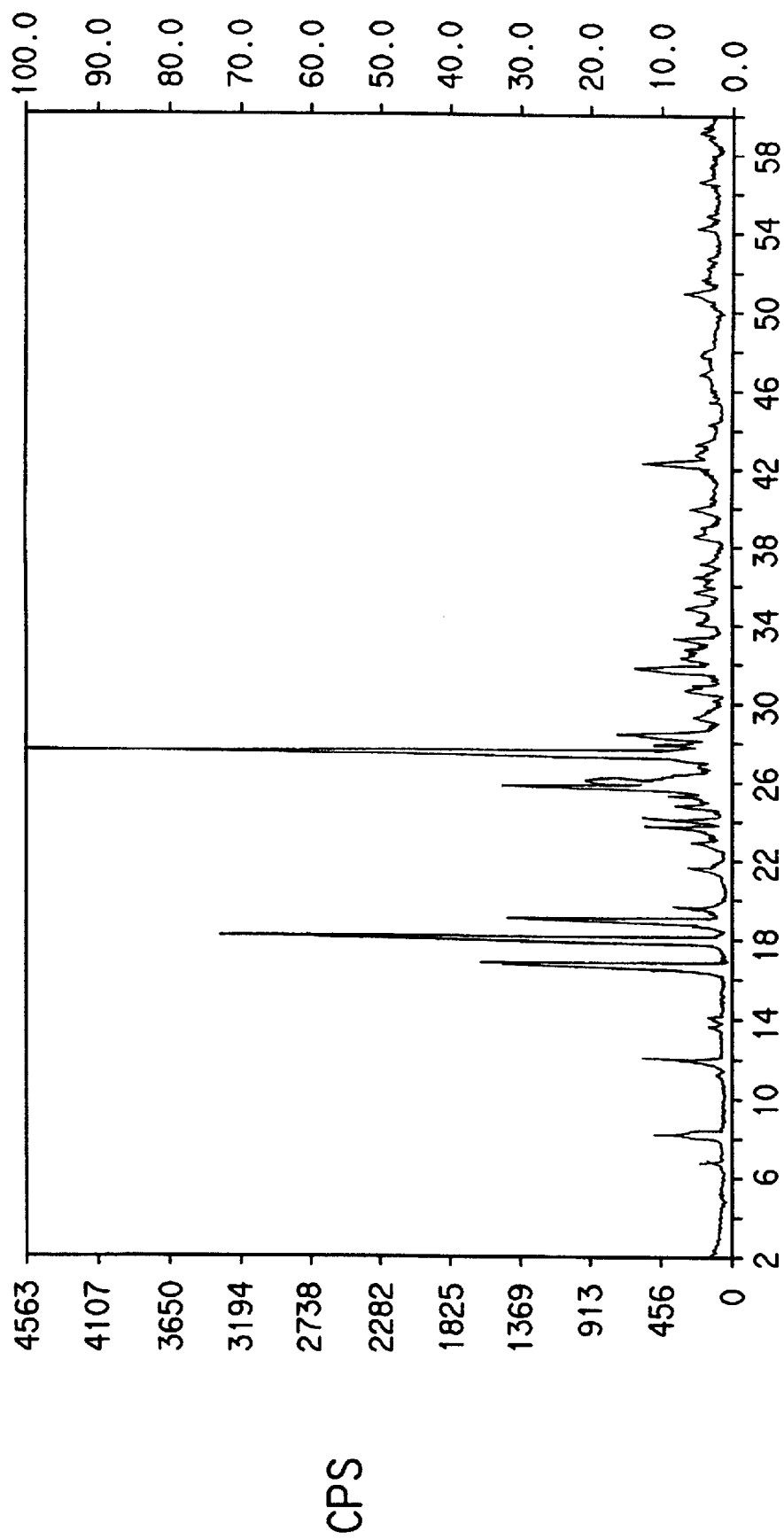
FIG. 3 is an X-ray diffraction pattern of commercially available melamine pyrophosphate of brand B.
Figure 4:
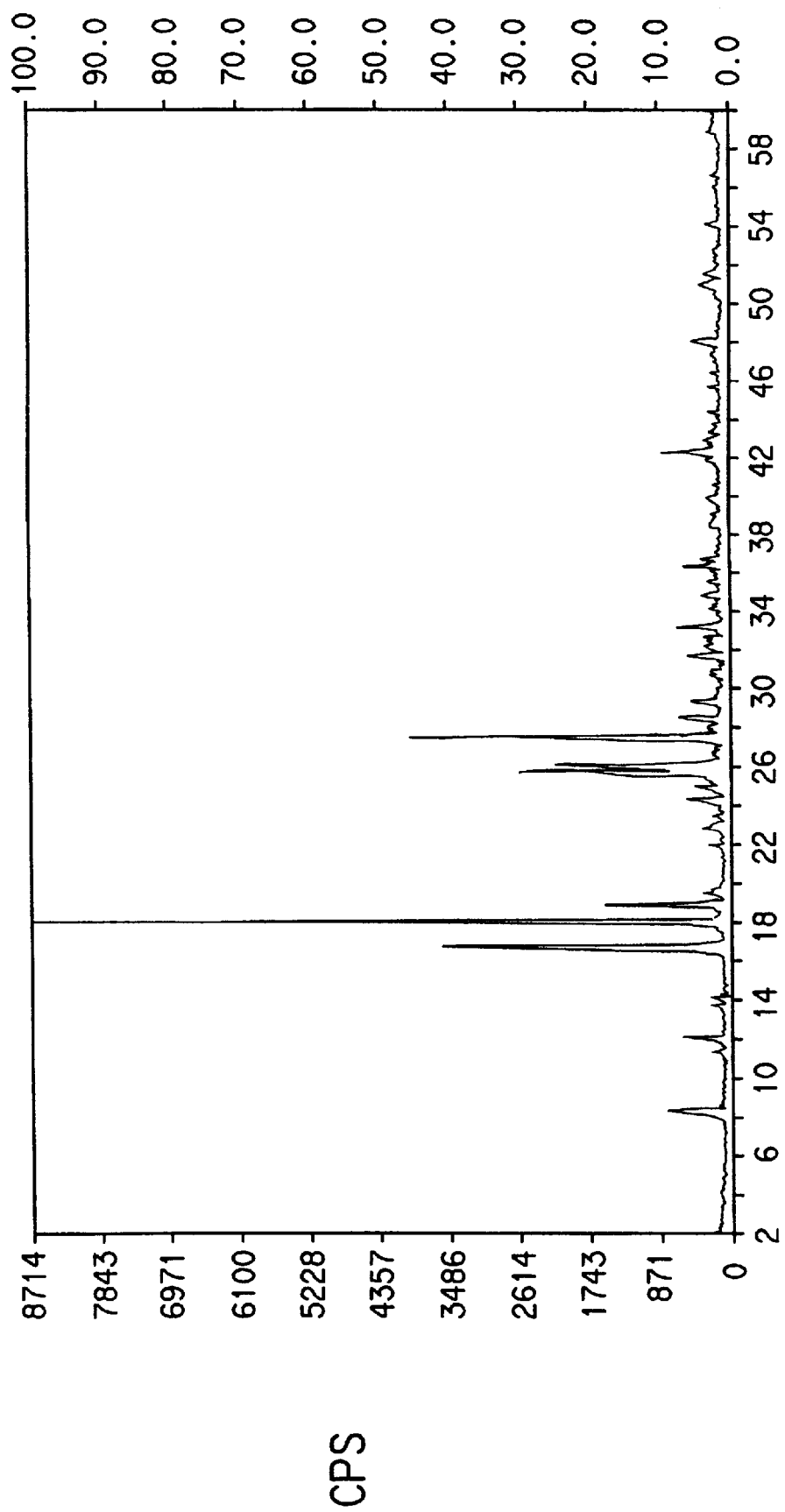
FIG. 4 is an X-ray diffraction pattern of commercially available melamine pyrophosphate of brand C.

A powder X-ray diffraction pattern was obtained for the product melamine pyrophosphate IX and is depicted in FIG. 1. The ratio of the diffraction peak intensity at powder diffraction angle 8.2 (Peak A) to the diffraction peak intensity at powder diffraction angle 17.9 (Peak B) was 0.37. Powder X-ray diffraction patterns were obtained for commercially available brands A, B, and C of melamine pyrophosphate and are depicted in FIGS. 2, 3 and 4, respectively. The above described ratio of Peak A and Peak B for brand A was 0.16, for brand B was 0.13, and for brand C was 0.08. Thus, the product of Example 1 represents a distinct crystallographic configuration of melamine pyrophosphate. A thermogravimetric analysis of this product is depicted in FIG. 5.

Example 2

Polyamide Extrusions

ZYTEL® 101 nylon 6,6 resin, the product of Example 1, ACRAWAX and dodecanedioic acid were mixed and extruded on a 30 mm extruder. The barrel temperatures were set at 260°C to 270°C. The extrusion rate was 30 lb/hr (13.6 kg/hr) with PPG 3540 glass reinforcing material added at 20 to 25 lb/hr (9.1to 11.3 kg/hr). The final composition was 28% melamine pyrophosphate IX (prepared according to Example 1), 25% PPG 3540 glass reinforcing agent, 0.25% ACRAWAX C, 0.25% dodecanedioic acid, and 46.5% ZYTEL® 101 nylon 6,6resin. Bars were molded on a standard 6 oz. (170 g) molding machine with temperature settings of 260°C. The flammability rating by Test Method 2 was UL-94 V-0 for $\frac{1}{16}$inch (1.6 mm) bars.

Example 3

Polyester Extrusions

RYNITE® 3934 polyethylene terephthalate resin, the product of Example 1, LOXIOL, and EPON were mixed and extruded as in Example 2except that PPG 3563 glass reinforcing material was substituted for PPG 3540.The final composition was 26% melamine pyrophosphate IX (prepared according to Example 1), 20% PPG 3563 glass reinforcing agent, 0.5% LOXIOL, 0.5% EPON, and 53% RYNITE® polyethylene terephthalate resin. The bars were molded as described in Example 2. The flammability rating was UL-94 V-0 for $\frac{1}{16}$ inch (1.6 mm) bars.

Example 4

Polyolefin/Polyamide Blend Extrusion

Polypropylene, ZYTEL® 101 nylon 6,6 resin, the product of Example 1,dodecanedioic acid, and ACRAWAX C were mixed and extruded as in Example 2, except that the PPG 3540 glass reinforcing material was omitted. The final composition was 33% melamine pyrophosphate IX (prepared according to Example 1), 33.5% polypropylene (from Lyondell, Houston, Tex.), and 33% ZYTEL® 101, with 0.5% each of dodecanedioic acid and ACRAWAX C.

Bars were molded as described in Example 2. The flammability rating by Test Method 2 was UL-94 V-0 for 1/16 inch (1.6 mm) bars.

Example 5

Polyolefin Extrusion

Polypropylene, the product of Example 1, and dipentaerythritol were mixed and extruded as in Example 4 except that the barrel temperatures were set at 200°C to 220°C. The final composition was 40% melamine pyrophosphate IX (prepared according to Example 1), 5% dipentaerythritol, and 55% polypropylene. Bars were molded as described in Example 2. The flammability rating was UL-94V-0 for 1/16 inch (1.6 mm) bars.

Example 6

Polyamide Extrusion with Coated Melamine Pyrophosphate IX

A1100 silane coupling agent was coated onto melamine pyrophosphate IX by spraying a solution of 0.6 weight % A1100 (relative to the weight of the melamine pyrophosphate IX) in methanol onto the melamine pyrophosphate IX contained in a large plastic bag with intermittent shaking to distribute the A1100 uniformly over the melamine pyrophosphate IX. The coated melamine pyrophosphate IX was placed a vacuum oven at 100°C for 4 hours to remove the methanol. Samples were mixed and extruded as in Example 2, except that the coated melamine pyrophosphate IX was substituted. The final composition was 28% melamine pyrophosphate IX coated with A1100, 25% PPG 3540 glass reinforcing agent, 0.25% ACRAWAX C, 0.25% dodecanedioic acid, and 46.5% ZYTEL® 101 nylon 6,6 resin. Bars were molded as in Example 2. The flammability rating was UL-94 V-0 for 1/16 inch (1.6 mm) bars. The elongation was 15% higher than in Example 2 as a result of the A1100 coating. The A1100 coating improved the compatibility of the melamine pyrophosphate IX with the nylon 6,6.

Example 7

Comparative Testing of Polyamide Extrusions with

Coated Melamine Pyrophosphate IX

Seven batches of melamine pyrophosphate IX, designated MPP IX 1–3 and MPP IX 5–8, were prepared as in Example 1 and extrusions prepared after coating the MPP IX coated with 0.6% by weight of A1100 according to the method of Example 6. The final extruded composition in each case was 51.5% ZYTEL® 101, 28% MPP IX coated with 0.6% A1100, 20% glass, 0.25% dodecanedioic acid, and 0.25% ACRAWAX C lubricant by weight. Extrusion bar thicknesses were 0.125 inch (0.318 cm) for tensile strength measurements and 0.03125 inch (0.7938 cm) for the UL94 flammability tests. The extruded bars were tested for tensile strength by Test Method 4 and UL94 flammability test by Test Method 2. Corresponding test bars were prepared substituting two commercial samples of MPP, also coated with 0.6% A1100. The test results are shown in Table 2.

TABLE 2

Strength, Elongation, and Flammability Results

| MPP Sample | strength kpsi (MPa) | Elongation (%) | Flammability (V-O, flaming time, s) |
|---|---|---|---|
| MPP IX 1 | 22.2 (153) | 2.5 | 12.5 |
| MPP IX 2 | 21.7 (150) | 2.6 | 14 |
| MPP IX 3 | 21.7 (150) | 2.5 | 33.5 |
| MPP IX 5 | 20.7 (143) | 2.4 | 16.5 |
| MPP IX 6 | 21.6 (149) | 2.6 | 12 |
| MPP IX 7 | 21.2 (146) | 2.4 | 11 |
| MPP IX 8 | 20.5 (141) | 2.2 | 22 |
| Mean values | 21.4 (148) | 2.48 | 21.7 |
| Comparative Example B | 19.7 (136) | 2.3 | 32 |
| Comparative Example C | 20.6 (142) | 2.4 | 33 |
| Mean values | 20.2 (139) | 2.35 | 32.5 |

Table 2 shows the superior physical properties and flammability performance of MPP IX prepared according to the process of the present invention compared with commercial MPP prepared according to the prior art.

What is claimed is:

1. A process for preparation of a melamine condensed phosphate comprising the steps of:
   a) contacting a solution of an alkali metal condensed phosphate with an acidic ion exchange resin at a temperature of 0°C to ambient to yield condensed phosphoric acid, and
   b) adding the condensed phosphoric acid to a slurry or suspension of melamine at a temperature of 0°C to ambient to yield the corresponding melamine condensed phosphate.

2. The process of claim 1 wherein the alkali metal condensed phosphate is tetrasodium pyrophosphate or tetrapotassium pyrophosphate.

3. The process of claim 1 wherein the melamine condensed phosphate is melamine pyrophosphate.

4. The process of claim 3 wherein the molar ratio of alkali metal condensed phosphate to melamine is 0.5 to 1.

* * * * *